United States Patent [19]

Penke et al.

[11] 4,102,878

[45] Jul. 25, 1978

[54] PROCESS FOR THE PREPARATION OF THE CHOLECYSTOKININ-PANCREOZYMIN OCTAPEPTIDE AMIDE SULFATE ESTER

[75] Inventors: Botond Penke; Lajos Balaspiri, both of Szeged, Hungary; Péter Pallai, Rockville, Md.; Kálmán Kovács, Szeged, Hungary; Vince Varró, Szeged, Hungary; János Lonovics, Szeged, Hungary; László Varga, Szeged, Hungary; György Dobó, Budapest, Hungary; Géza Iványi, Taksony, Hungary; Lajos Kovács, Budapest, Hungary; Miklós Lőw, Budapest, Hungary; Judit Lőw, née Kaloczy, Budapest, Hungary

[73] Assignee: Richter Gedeon Vegyeszeti Gyar Rt., Budapest, Hungary

[21] Appl. No.: 792,043

[22] Filed: Apr. 28, 1977

[30] Foreign Application Priority Data

May 5, 1976 [HU] Hungary .................... RI 589

[51] Int. Cl.² .......................................... C07C 103/52
[52] U.S. Cl. ............................................. 260/112.5 R
[58] Field of Search ................................ 260/112.5 R

[56] References Cited

U.S. PATENT DOCUMENTS 3,892,726  7/1977  Ondetti .................. 260/112.5 R

OTHER PUBLICATIONS

J. Plusec, et al., J. Med. Chem., 1970, vol. 13, pp. 349–352.
M. Onetti, et al., J. Amer. Chem. Soc. 92, 1970, pp. 195–199.

Primary Examiner—Delbert R. Phillips
Attorney, Agent, or Firm—Karl F. Ross

[57] ABSTRACT

A process for the preparation of L-aspartyl-(O-sulfato-L-tyrosyl)-L-methionyl-glycyl-L-tryptophyl-L-methionyl-L-aspartyl-L-phenylalanine amide, which comprises treating the protected octapeptide amide of the general formula (II)

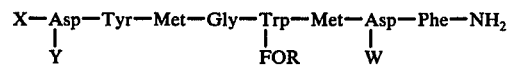

wherein
X is BOC, Cbz or Ddz,
Y is O'Bu, OBzl or OH and
W is O'Bu, OBzl or OH, in the presence of an ether with an excess of the complex compound of sulfur trioxide and a tertiary amine containing at least one alkyl group, converting the obtained sulfate ester of the protected octapeptide amide into an alkali metal salt and simultaneously removing the formyl group from the tryptophan unit by reacting the sulfate ester with an alkali metal hydroxide, and then splitting off the remaining protective groups by acidolysis.

5 Claims, No Drawings

PROCESS FOR THE PREPARATION OF THE CHOLECYSTOKININ-PANCREOZYMIN OCTAPEPTIDE AMIDE SULFATE ESTER

The invention relates to a new process for the preparation of the cholecystokinin-pancreozymin octapeptide amide sulfate ester of the formula (I)

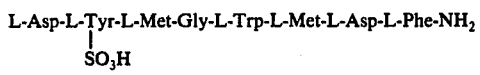

Ivy and Oddberg [Amer. J. Physiol. 86, 599 (1928)] isolated in 1928 from the mucous membrane of intestines a substance which caused the contraction of the gall-bladder and which they called "cholecystokinin". Harper and Raper [J. Physiol. 102, 115 (1943)] described later a substance called by these authors "pancreozymin", and isolated from extracts of intestinal mucous membranes, which increased the enzyme secretion of the pancreas. Mutt and Jorpes [Acta Chem. Scand. 18, 2408 (1964)] have shown that both biological effects are caused by the same substance, a hormone called by these authors "cholecystokinin-pancreozymin". The same authors have also determined the amino acid sequence of this hormones [Biochem. J. 125, 678 (1971)]: Lys-Ala-Pro-Ser-Gly-Arg-Val-Ser-Met-Ile-Lys-Asn-Leu-Gln-Ser-Leu-Asp-Pro-Ser-His-Arg-Ile-Ser-Asp-Arg-Asp-Tyr($SO_3H$)-Met-Gly-Trp-Met-Asp-Phe-$NH_2$. Ondetti and Pluscec [J. Am. Chem. Soc. 92, 195 (1970); J. Med. Chem. 13, 349 (1970); see also: Hungarian Patent Specifications No. 162,875 and 163,626] synthesized the sulfate ester of C-terminal octapeptide amide of cholecystokinin-pancreozymin and a series of analogous compounds, and have found that the octapeptide amide sulfate ester as well as some analogous compounds have a considerably higher activity than the complete molecule of cholecystokinin-pancreozymin.

This octapeptide amide sulfate ester, when administered in doses of cca. $10^{-6}$ mg/kg., is a useful diagnostic means for the examination of the contraction of the gall bladder and of the pancreatic secretion (cf. Hungarian Patent Specification No. 162,875). More recent investigations have also revealed that the said octapeptide amide sulfate ester exterts a strong relaxing action on the muscle sphincter Oddii; thus this compound can be used with good results to alleviate the spasms occuring after gall-bladder operations [see M.A. Ondetti, B. Rubin, S. Engel: J. Amer. Digestive Diseases 15, 149 (1970)].

Ondetti et al. described also a process for the preparation of the octapeptide amide sulfate ester [Hungarian Patent Specification No. 162,875, German DOS 1,922,185, J. Am. Chem. Soc. 92, 195 (1970)]. The protected octapeptide amide and the intermediate compounds used in the synthesis thereof are prepared by the known methods of peptide chemistry. Then the tyrosine unit is sulfatized in known manner by treatment with the complex compound of pyridine and sulfur trioxide and finally the protective groups are removed by acidolysis with trifluoroacetic acid. Yields about 30 percent can be obtained with this process. According to another method described by the same authors the free octapeptide amide was treated at low temperature with concentrated sulfuric acid or with a mixture of sulfuric acid and potassium hydrogen sulfate. By this method the sulfate ester of the octapeptide amide is obtained in quite poor yields, about 10 percent, and a large amount of a peptide containing sulfonated tyrosine is obtained as by-product.

It has been found that the reaction rate of sulfatizing of the protected octapeptide amide can be considerably increased, if a complex of sulfur trioxide with a tertiary amine containing at least one alkyl group is used instead of the said complex of sulfur trioxide with pyridine, and the treatment with this complex is carried out in the presence of an ether. Further it has been observed that the $N^i$-formyl group proposed in the literature [D. Yamashiro, C.H. Li: J. Org. Chem. 38, 2594 (1973)] for protecting tryptophan against t-butylation and oxidation reactions, can be used surprisingly also against a sulfonating reaction during the sulfonic acid treatment to form the sulfate ester on the tyrosine group of the peptide. Finally it has been found in performing the acidolytic removal of the protective groups that the undesired acid hydrolysis of the sulfate ester group does not take place even in the course of a prolonged acidolytic treatment for several hours, if the acidolytic removal of the protective groups is performed by reacting an alkali metal salt of the protected octapeptide amide with an excess of trifluoroacetic acid or mercaptoethane sulfonic acid. By combining these three new features of the preparation method, substantially better results can be achieved, than by the process known from the literature.

The subject matter of the invention is thus a process for the preparation of L-aspartyl-(O-sulfato-L-tyrosyl)-L-methionyl-glycyl-L-tryptophyl-L-methionyl-L-aspartyl-L-phenylalanine amide. This sulfate ester of the C-terminal octapeptide amide of cholecystokinin-pancreozymin is prepared according to the invention by treating the protected octapeptide amide of the general formula (II)

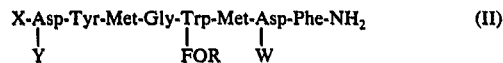

wherein
X is BOC, Cbz or Ddz,
Y is O$^t$Bu, OBzl or OH and
W is O$^t$Bu, OBzl or OH in the presence of an ether with an excess of the complex compound of sulfur trioxide and a tertiary amine containing at least one alkyl group, converting the obtained sulfate ester of the protected octapeptide amide into an alkali metal salt and simultaneously removing the formyl group from the tryptophan unit by reacting the sulfate ester with an alkali metal hydroxide, and then splitting off the remaining protective groups by acidolysis.

The symbols used to describe the peptides and the amino acid units thereof are the same as used in the international IUPAC-IUB nomenclature, cf. J. Biol. Chem. 247,977 (1972). The other symbols and abbreviations used in the above definitions and in the following parts of the present specification and claims have the following meanings:
BOC = tert.-butyloxycarbonyl,
Cbz = carbobenzoxy,
Ddz = α,α-dimethyl-3,5-dimethoxybenzyloxycarbonyl,
O$^t$Bu = tert.-butyloxy,
OBzl = benzyloxy,
FOR = formyl.

The protected octapeptide amide of the general formula (II) used as starting material can be prepared in per se known manner by condensation of the proper peptide fragments or by building up the peptide by stepwise coupling the amino acids; the known mixed anhydride, azide, active ester or dicyclohexyl carbodiimide methods may be used to perform the said synthesis steps. One may apply also the so-called solid phase synthesis method, wherein the peptide attached through the terminal carboxyl group to a polymer compound is built up by starting from the C-terminal amino acid attached to the said polymer compound and coupling thereto the further amino acid stepwise in the proper order of sequence.

In the process of the invention, the functional groups not taking part in the reaction are to be protected by blocking them with protective groups which may be easily removed after the reaction by known methods, especially by hydrolysis, acidolysis, hydrazinolysis or reduction. The indole nitrogen atom of the tryptophan unit is protected by a formyl group; the use of this particular protecting group at this nitrogen atom has the advantage that it prevents the formation of tert.-butyl derivatives during the acidolysis reactions performed in the course of the synthesis of the octapeptide amide.

The other protective groups used in the course of the synthesis of the octapeptide amide may be those mentioned in the above definition of the general formula (II). By choosing proper combinations of these protective groups the protective group of the starting compound of the general formula (II) can be made removable by known methods, as hydrolysis, acidolysis, hydrazinolysis or reduction either simultaneously in a single step, or, if desired, selectively in a desired order of sequence.

According to a preferred method of performance of the process of the invention, a protected octapeptide amide of the formula (II) is used as starting material, wherein X is BOC and Y is O$^t$Bu. This protected octapeptide amide is converted into the sulfate ester by treating it with a dioxane solution of a 20 to 30-fold excess of the complex compound of N-methyl morpholine and sulfur trioxide. (This complex can be prepared in known manner, e.g. by reacting the tertiary amine with chlorosulfonic acid.) The obtained protected sulfate ester is then converted into the sodium salt thereof by reacting it in aqueous solution with two mole equivalents of sodium hydroxide; by this treatment with sodium hydroxide also the formyl protective group is simultaneously removed from the tryptophan unit of the protected octapeptide amide. The final step is then the removal of the BOC and O$^t$Bu protective groups by treating the octapeptide amide sulfate ester with either a mixture of 70-85% volume of trifluoroacetic acid, 5-10% by volume of mercaptoethanol, 5-10% by volume of water and 5-10% by volume of anisol, or with a 3 molar solution of mercaptoethane sulfonic acid in glacial acetic acid. The end product obtained by this method is general sufficiently pure and free from by-products; it may be, however, purified if necessary, by chromatography of a silica gel column, with a mixture of equal portions of ethyl acetate and a 20:6:11 mixture of pyridine, acetic acid and water.

The starting material of the process of the invention the protected octapeptide amide of the formula (II), e.g. the amide BOC-Asp(O$^t$Bu)-Tyr-Met-Gly-Trp(FOR)-Met-Asp-Phe-NH$_2$ can be prepared e.g. in the following way:

The tripeptide amide L-methionyl-L-asparalyl-L-phenylalanyl-amide is acylated with N-tert.-butoxycarbonyl-N$^i$-formyl-L-tryptophan-pentachlorophenyl ester, the N-tert.-butyloxycarbonyl protective group is then removed from the obtained protected tetrapeptide amide in the usual way, by treatment with a mixture of N hydrochloric acid and glacial acetic acid. The obtained free tetrapeptide amide is then acylated with tert.-butyloxycarbonyl-L-methionyl-glycine-pentachlorophenyl ester. The obtained protected hexapeptide amide is isolated in the usual manner, and after removal of the protective group acylated with tert.-butyloxycarbonyl-L-tyrosine-trichlorophenyl ester. The product is again isolated and the protective group is removed in the usual way, and finally the obtained heptapeptide amide is acylated with tert.-butyloxycarbonyl-β-tert.-butyl-L-aspartic acid pentachlorophenyl ester, to obtain the desired protected octapeptide amide.

The octapeptide amide sulfate ester of the formula (I) prepared according to the invention, when administered to dogs, causes the contraction of the gall bladder and the relaxation of the muscle sphincter Oddii in i.v. doses of 2 to 10 mg/kg. The product can be used both for diagnostic and therapeutical purposes. For parenteral administration the octapeptide amide sulfate ester can be converted in known manner into salts formed with therapeutically acceptable bases, e.g. with sodium, potassium or ammonium hydroxide or with lysine or histidine.

The process of the invention and the preparation of the starting protected octapeptide amide is illustrated in more detail by the following Example. The melting points given in the Example were measured in a Dr. Tottoli's apparatus (manufacturer: Büchi, Switzerland). The thin layer chromatographic measurements ($R_f$-values) were made on silica gel plates, by the use of the following solvent systems (if not stated otherwise):

(1) 1 part by volume of ethyl acetate and 1 part by volume of the 20:6:11 mixture of pyridine, acetic acid and water;
(2) 6 parts by volume of ethyl acetate and 4 parts by volume of the 20:6:11 mixture of pyridine, acetic acid and water;
(3) 8 parts by volume of ethyl acetate and 2 parts by volume of the 20:6:11 mixture of pyridine, acetic acid and water.

EXAMPLE

L-Aspartyl(O-sulfato-L-tyrosyl)-L-methionyl-glycyl-L-tryptophyl-L-methionyl-L-aspartyl-L-phenylalanine amide.

1.6 ml. (25 mmole) of chlorosulfonic acid are dissolved in 2 ml. of chloroform, cooled to 10° C and at this temperature, the solution of 3.3 ml. (30 mmole) of N-methyl-morpholine in the mixture of 3 ml. of dioxane and 3 ml. of dimethyl formamide are added under vigorous stirring. After five minutes the solution of 1.25 g. (1.0 mmole) of tert.-butyloxycarbonyl-β-tert.-butyl-L-aspartyl-L-tyrolsyl-L-methionyl-glycyl-(N$^i$-formyl-L-tryptophyl)-L-methionyl-L-aspartyl-L-phenylalanine amide in 8 ml. of dimethyl formamide are added to the obtained suspension. The mixture is stirred at room temperature for three hours, then cooled to 0° C and 5 ml. of aqueous 4 N sodium hydroxide solution are added thereto under stirring. The obtained solution is evaporated to dryness, the evaporation residue is triturated with 20 ml. of water cooled to 0° C, the solid product is separated by filtration and washed with 2 × 20 ml. of water and then with 20 ml. of ether. The thus obtained crude protected octapeptide amide sulfate ester is then dissolved in the mixture of 20 ml. of methanol and 20 ml. of water, the pH-value of the solution is adjusted to 8 by adding 2 ml. of aqueous 4 N sodium hydroxide solution. After 20 minutes the solution is evaporated, the residue is triturated with the 1:1 mixture of acetone and ether, filtered and washed with ether. The obtained product is dissolved in a mixture of 8 ml. of trifluoroacetic acid, 1 ml. of water, 1 ml. of anisol and 1 ml. of mercaptoethanol cooled previously to 0° C, the solution is allowed to stand for three hours at 15° C to 20° C, then it is poured into 100 ml. of ether under stirring, and the precipitated product is filtered. Thus 0.90 g. of the desired octapeptide amide sulfate ester (77% of the theoretical yield) are obtained, $R_f(1) = 0.4$.

The product can be purified, if necessary, by chromatography on a column containing 80 g. of silica gel; the column is eluted with a 37:20:6:11 mixture of ethyl acetate, pyridine, glacial acetic acid and water.

The tert.-butyloxycarbonyl-$\beta$-tert.-butyl-L-aspartyl-L-tyrosyl-L-methionyl-($N^i$-formyl-L-tryptophyl)-L-methionyl-L-aspartyl-L-phenylalanine amide used as starting material in the process of the above Example is prepared preferably in the following way:

(a)
N-tert.-Butyloxycarbonyl-$N^i$-formyl-L-tryptophyl-L-methionyl-L-aspartyl-L-phenylalanine amide 22.34 g. (50 mmole) of L-methionyl-L-aspartyl-L-phenylalanine amide hydrochloride (I.M. Davey, A.H. Laird, I.S. Morley: J. Chem. Soc. 1966, 555) are dissolved in 200 ml. of dimethyl formamide, then 11.1 ml. (100 mmole) of N-methyl-morpholine and 28.9 g. (50 mmole) of N-tert.butyloxycarbonyl-$N^i$-formyl-L-tryptophane pentachlorophenyl ester are added to the solution. The pH-value of the solution is adjusted to 7 to 7.5 by adding further N-methyl-morpholine thereto. After 12 hours the reaction mixture is evaporated to a volume of 50 ml., and then poured under vigorous mixing at 0° C into the mixture of 200 ml. of an aqueous 5% KHSO$_4$ solution and 100 ml. of peroxide-free ether. The obtained precipitate is separated by filtration, washed with ether and dried. 26 g. of pure N-tert.-butyloxycarbonyl-$N^i$-formyl-L-tryptophyl-L-methionyl-L-aspartyl-L-phenylalanine amide (72% of the theoretical yield) are obtained; m.p. 209° C; $[\alpha]_D^{20} = -22°$ (c = 2, dimethyl formamide); $R_f(2) = 0.7$.

(b) tert.-Butyloxycarbonyl-L-methionyl-glycine pentachlorophenyl ester 1.9 g. (6.2 mmole) of tert.-butyloxycarbonyl-L-methionyl-glycine [M.A. Ondetti, I. Phuscec, E.F. Sabo, J.T. Sheehan, N-Williams; J. Am. Chem. Soc. 92, 195 (1970)] and 1.92 g. (7.2 mmole) of pentachlorophenol are dissolved in 31 ml. of dimethyl formamide. The solution is cooled to 0° C, the solution of 1.41 g. (6.85 mmole) of dicyclohexyl carbodiimide in 6.2 ml. of dimethyl formamide is added dropwise under stirring and the mixture is stirred for a further hour at the same temperature. The mixture is allowed to stand over night; on the following day the precipitated dicyclohexyl urea is filtered off and the filtrate is evaporated to dryness under reduced pressure. The evaporation residue is triturated with ether, the product filtered, washed with a minor amount of ether and recrystallized from a 15-fold amount of ether. 2.19 g. of tert.-butyloxycarbonyl-L-methionyl-glycine pentachlorophenyl ester (63.6% of the theoretical yield) are obtained; m.p. 169°–171° C; $R_f$(in the 8:2 mixture of chloroform and ethanol) = 0.8.

(c)
tert.-Butyloxycarbonyl-L-methionyl-glycyl-($N^i$-formyl-L-tryptophyl)-L-methionyl-L-aspartyl-L-phenylalanine amide.

25.3 g. (35 mmole) of N-tert.-butyloxycarbonyl-$N^i$-formyl-L-tryptophyl-L-methionyl-L-aspartyl-L-phenylalanine amide are dissolved in 120 ml. of an N/1 solution of hydrochloric acid in glacial acetic acid. After standing for 90 minutes the solution is evaporated to the half of its original volume, and the obtained tetrapeptide amide hydrochloride is precipitated by the addition of 500 ml. of ether. The precipitate is separated by filtration, washed with ether and dried; 20.3 g. of $N^i$-formyl-L-tryptophyl-L-methionyl-L-aspartyl-L-phenylalanine amide hydrochloride (88% of the theoretical yield) are obtained; m.p. 207°–209° C.

3.3 g. (5 mmole) of the thus obtained tetrapeptide amide hydrochloride and 2.77 g. (5 mmole) of tert.-butyloxycarbonyl-L-methionyl-glycine pentachlorophenyl ester are dissolved in 25 ml. of dimethyl formamide, and 1.11 ml. (10 mmole) of N-methyl-morpholine is added to the solution. After standing for 24 hours, the mixture is evaporated in vacuo to the half of its original volume and poured under vigorous stirring into the mixture of 50 ml. of an aqueous 5% KHSO$_4$ solution and of 30 ml. of ether. The obtained precipitate is separated by filtration, washed with water and then with ether and dried. 3.7 g. of the protected hexapeptide amide tert.-butyloxycarbonyl-L-methionyl-glycyl-($N^i$-formyl-L-tryptophyl)-L-methionyl-L-aspartyl-L-phenylalanine amide (81% of the theoretical yield) are obtained; m.p. 175°–179° C; $R_f(3) = 0.45$.

(d)
tert.-Butyloxycarbonyl-L-tyrosyl-L-methionyl-glycyl-($N^i$-formyl-L-tryptophyl)-L-methionyl-L-aspartyl-L-phenylalanine amide 3.65 g. (4 mmole) of tert.-butyloxycarbonyl-L-methionyl-glycyl-($N^i$-formyl-L-tryptophyl)-L-methionyl-L-aspartyl-L-phenylalanine amide are dissolved in 15 ml. of an N/1 solution of hydrochloric acid in glacial acetic acid. After standing for 30 minutes the hydrochloride of the hexapeptide amide is precipitated by the addition of 300 ml. of ether, the precipitate is separated by filtration, washed with ether and dried. 3.2 g. of L-methionyl-glycyl-($N^i$-formyl-L-tryptophyl)-L-methionyl-L-aspartyl-L-phenylalanine amide hydrochloride (94% of the theoretical yield) are obtained; m.p. 130°–132° C.

3.2 g. (3.77 mmole) of the above hexapeptide amide hydrochloride and 1.84 g. (4 mmole) of tert.-butyloxycarbonyl-L-tyrosine 2,4,5-trichlorophenyl ester are dissolved in 25 ml. of dimethyl formamide, and 0.9 ml. (8 mmole) of N-methyl-morpholine are added to the solution. The reaction mixture is allowed to stand for 24 hours, it is then evaporated to the half of its original volume and poured under stirring into the mixture of 50 ml. of an aqueous 5% KHSO$_4$ solution and 30 ml. of ether. The obtained precipitate is separated by filtration, washed with water and then with ether and dried. 3.7 g. of the protected heptapeptide amide tert.-butyloxycarbonyl-L-tyrosyl-L-methionyl-glycyl-($N^i$-formyl-L-tryptophyl)-L-methionyl-L-aspartyl-L- phenylalanine amide (92% of the theoretical yield) are obtained; $R_f(3) = 0.55$.

(e)

tert.-Butyloxycarbonyl-β-tert.-butyl-aspartyl-L-tyrosyl-L-methionyl-glycyl-(N$^i$-formyl-L-tryptophyl)-L-methionyl-L-aspartyl-L-phenylalanine amide 3.7 g. (3.45 mmole) of tert.-butyloxycarbonyl-L-tyrosyl-L-methionyl-glycyl-(N$^i$-formyl-L-tryptophyl)-L-methionyl-L-aspartyl-L-phenylalanine amide are dissolved in 15 ml. of an N/1 hydrochloric acid solution in glacial acetic acid. After standing for 30 minutes 300 ml. of ether are added to the solution, the precipitated heptapeptide amide hydrochloride is separated by filtration, washed with ether and dried. 3.45 g. of L-tyrosyl-L-methionyl-glycyl-(N$^i$-formyl-L-tryptophyl)-L-methionyl-L-aspartyl-L-phenylalanine amide hydrochloride (99% of the theoretical yield) are obtained.

3.04 g. (3.0 mmole) of the above heptapeptide amide hydrochloride and 1.7 g. (3.17 mmole) of tert.-butyloxycarbonyl-β-tert.-butyl-aspartic acid pentachlorophenyl ester are dissolved in 20 ml. of dimethyl formamide and 0.7 ml. (6.3 mmole) of N-methyl-morpholine are added to the solution. The reaction mixture is allowed to stand for 24 hours and then it is poured into the mixture of 50 ml. of an aqueous 5% KHSO$_4$ solution and 30 ml. of ether. The obtained precipitate is separated by filtration, washed with water and then with ether and dried. 3.01 g. of the protected octapeptide amide tert.-butyloxycarbonyl-β-tert.-butyl-L-aspartyl-L-tyrosyl-L-methionyl-glycyl-N$^i$-formyl-L-tryptophyl)-L-methionyl-L-aspartyl-L-phenylalanine amide (80% of the theoretical yield) are obtained; $R_f(3) = 0.7$.

What we claim is:

1. A process for the preparation of L-aspartyl-(O-sulfato-L-tyrosyl)-L-methionyl-glycyl-L-tryptophyl-L-methionyl-L-aspartyl-L-phenylalanine amide, which comprises treating the protected octapeptide amide of the formula

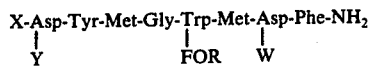

wherein
X is BOC, Cbz or Ddz,
Y is O$^t$Bu, OBzl or OH and
W is O$^t$Bu, OBzl or OH,
a catalytically effective ether solvent in the presence of an ether with excess of a complex compound sulfur trioxide and a tertiary amine containing at least one alkyl group, converting the obtained sulfate ester of the protected octapeptide amide into an alkali metal salt and simultaneously removing the formyl group from the tryptophan unit by reacting the sulfate ester with an alkali metal hydroxide, and then splitting off the remaining protective groups by acidolysis.

2. A process as defined in claim 1, wherein the complex compound of sulfur trioxide and N-methyl-morpholine is used as complex compound of sulfur trioxide and a tertiary amine containing at least one alkyl group, and dioxane is used as the ether.

3. A process as defined in claim 1, wherein the amino group of the N-terminal aspartic acid unit of the starting protected octapeptide amide is protected by a tert.-butyloxycarbonyl group and the β-carboxyl group thereof is protected by a tert.-butyl ester group.

4. A process as defined in claim 1, wherein the obtained protected octapeptide amide sulfate ester is converted into the sodium salt and the formyl protective group of the tryptophan unit is simultaneously split off by treating the said sulfate ester with two mol-equivalents of sodium hydroxide in aqueous solution.

5. A process as defined in claim 1, wherein the protective group of the obtained protected octapeptide amide sulfate ester disodium salt are removed by treating the said salt with a mixture of 70 to 85% by volume of trifluoroacetic acid, 5–10% by volume of mercaptoethanol, 5–10% by volume of water and 5–10% by volume of anisol or with a 3 molar solution of mercaptoethane sulfonic acid in glacial acetic acid.

* * * * *